US009155878B2

(12) United States Patent  (10) Patent No.: US 9,155,878 B2
Goode et al.  (45) Date of Patent: Oct. 13, 2015

(54) DEVICE FOR PREPARING AN IMPLANTED MEDICAL APPARATUS FOR EXTRACTION

(71) Applicant: Cook Medical Technologies LLC, Bloomington, IN (US)

(72) Inventors: Louis B. Goode, Cranberry Township, PA (US); Chun Kee Lui, Apollo, PA (US); Michael Wayne Emmert, Apollo, PA (US); Robert Booker, Vandergrift, PA (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 14/711,240

(22) Filed: May 13, 2015

(65) Prior Publication Data

US 2015/0238751 A1 Aug. 27, 2015

Related U.S. Application Data

(62) Division of application No. 13/716,975, filed on Dec. 17, 2012, now Pat. No. 9,055,930.

(51) Int. Cl.
*A61B 19/00* (2006.01)
*A61N 1/05* (2006.01)
*A61B 17/50* (2006.01)

(52) U.S. Cl.
CPC . *A61N 1/05* (2013.01); *A61B 17/50* (2013.01); *A61N 2001/0578* (2013.01)

(58) Field of Classification Search
CPC .................. A61B 17/221; A61B 2017/22035; A61B 17/00; A61B 17/3468; A61B 2017/00469; A61N 1/0488; A61N 2001/0578; A61N 1/056; A61F 2/95; A61F 2002/958; A61F 2/2427; A61F 2002/011
See application file for complete search history.

(56) References Cited

U.S. PATENT DOCUMENTS 2,147,160 A * 2/1939 Hagist et al. ................. 24/135 N
4,943,289 A * 7/1990 Goode et al. ...................... 606/1
(Continued)

FOREIGN PATENT DOCUMENTS

EP  1 903 957 B1  12/2011
JP  2-180248 A  7/1990
(Continued)

OTHER PUBLICATIONS

Search Report for EP Application No. EP 13 19 6293; dated Apr. 2, 2014; 10p.

(Continued)

*Primary Examiner* — Jonathan W Miles
*Assistant Examiner* — Chima Igboko
(74) *Attorney, Agent, or Firm* — Brinks Gilson & Lione

(57) ABSTRACT

A device for preparing an elongated implanted medical apparatus, such as a cardiac lead, for extraction from the body of a patient. The device includes a first handle and a second handle. At least the first handle has a surface for receiving the implanted apparatus therealong. A wire member having a first end and a second end is positioned to span a distance between the surface of the first handle, and the second handle. The wire member first end is removably engaged with the first handle, and the wire member second end is removably engaged with the second handle. The wire member is sized and arranged to enable the wire member to be wound around a length of the implanted apparatus to facilitate extraction of the apparatus with a lead extraction device.

5 Claims, 11 Drawing Sheets

(56) References Cited

U.S. PATENT DOCUMENTS

| | | | |
|---|---|---|---|
| 4,988,347 A | 1/1991 | Goode et al. | |
| 5,011,482 A | 4/1991 | Goode et al. | |
| 5,013,310 A | 5/1991 | Goode et al. | |
| 5,171,233 A * | 12/1992 | Amplatz et al. | 604/540 |
| 5,207,683 A | 5/1993 | Goode et al. | |
| 5,217,438 A * | 6/1993 | Davis et al. | 604/198 |
| 5,423,806 A | 6/1995 | Dale et al. | |
| 5,507,751 A | 4/1996 | Goode et al. | |
| 5,632,749 A | 5/1997 | Goode et al. | |
| 5,678,579 A * | 10/1997 | Meyer et al. | 132/323 |
| 5,697,936 A * | 12/1997 | Shipko et al. | 606/108 |
| 5,993,463 A * | 11/1999 | Truwit | 606/130 |
| 6,045,572 A * | 4/2000 | Johnson et al. | 606/232 |
| 6,136,005 A | 10/2000 | Goode et al. | |
| 6,156,055 A | 12/2000 | Ravenscroft | |
| 6,419,674 B1 | 7/2002 | Bowser et al. | |
| 6,517,550 B1 * | 2/2003 | Konya et al. | 606/113 |
| 6,687,548 B2 | 2/2004 | Goode | |
| 6,712,826 B2 | 3/2004 | Lui | |
| 7,076,305 B2 * | 7/2006 | Imran et al. | 607/40 |
| 7,359,756 B2 | 4/2008 | Goode | |
| 7,651,504 B2 * | 1/2010 | Goode et al. | 606/113 |
| 7,905,904 B2 * | 3/2011 | Stone et al. | 606/232 |
| 8,192,430 B2 | 6/2012 | Goode et al. | |
| 8,632,590 B2 * | 1/2014 | Cauthen et al. | 623/17.11 |
| 2004/0030335 A1 * | 2/2004 | Zenati et al. | 606/51 |
| 2004/0147958 A1 * | 7/2004 | Lam et al. | 606/232 |
| 2005/0049592 A1 * | 3/2005 | Keith et al. | 606/61 |
| 2005/0192591 A1 * | 9/2005 | Lui et al. | 606/108 |
| 2006/0235431 A1 | 10/2006 | Goode et al. | |
| 2007/0239280 A1 * | 10/2007 | Keith et al. | 623/17.16 |
| 2008/0103504 A1 * | 5/2008 | Schmitz et al. | 606/79 |
| 2008/0147084 A1 * | 6/2008 | Bleich et al. | 606/114 |
| 2009/0198282 A1 * | 8/2009 | Fielding et al. | 606/279 |
| 2009/0222021 A1 * | 9/2009 | Chang | 606/129 |
| 2009/0259260 A1 * | 10/2009 | Bentley et al. | 606/300 |
| 2009/0281579 A1 * | 11/2009 | Weaver et al. | 606/286 |
| 2010/0087857 A1 * | 4/2010 | Stone et al. | 606/232 |
| 2010/0222787 A1 | 9/2010 | Goode et al. | |
| 2010/0234862 A1 * | 9/2010 | Patel et al. | 606/151 |
| 2010/0292732 A1 * | 11/2010 | Hirotsuka et al. | 606/232 |
| 2010/0331883 A1 * | 12/2010 | Schmitz et al. | 606/249 |
| 2011/0109072 A1 * | 5/2011 | Ligouri et al. | 280/818 |
| 2011/0202137 A1 * | 8/2011 | Keith et al. | 623/17.16 |
| 2011/0213417 A1 * | 9/2011 | Foerster et al. | 606/232 |
| 2011/0230893 A1 * | 9/2011 | Barker | 606/129 |
| 2011/0237967 A1 * | 9/2011 | Moore et al. | 600/509 |
| 2011/0238078 A1 | 9/2011 | Goode et al. | |
| 2012/0029335 A1 | 2/2012 | Sudam et al. | |

FOREIGN PATENT DOCUMENTS

| | | |
|---|---|---|
| JP | 6-508274 A | 9/1994 |
| JP | 8-132778 A | 5/1996 |
| WO | WO 2006/113438 A3 | 10/2006 |

OTHER PUBLICATIONS

English language translation of Office Action for corresponding Japanese Application No. 2013-259223, which includes Record of Search for Prior Art Documents, dated Oct. 21, 2014, 3p.

* cited by examiner

DEVICE FOR PREPARING AN IMPLANTED MEDICAL APPARATUS FOR EXTRACTION

CROSS-REFERENCE TO RELATED APPLICATIONS

This application claims priority to U.S. Non-Provisional application Ser. No. 13/716,975, filed Dec. 17, 2012, and titled "Device for Preparing an Implanted Medical Apparatus for Extraction", the contents of which are incorporated herein by reference.

BACKGROUND

1. Technical Field

This invention relates to a device for facilitating the extraction of an implanted medical apparatus from the body of a patient. More particularly, the invention relates to a device for preparing an implanted elongated medical apparatus for extraction from a body passageway by exerting a compressive force along the proximal end of the elongated apparatus to hold the elements of the apparatus in place during the extraction procedure.

2. Background Information

A variety of medical treatments and surgical methods entail implanting a device, such as a pacemaker, in the body of a patient. A pacemaker is typically positioned in a subcutaneous tissue pocket in the chest wall of a patient. A pacemaker lead is implanted in the body of the patient to extend from the pacemaker through a vein into a chamber of the patient's heart. The lead comprises an elongated apparatus that includes one or more longitudinal cables, wires, coils, etc. (hereafter collectively referred to as "cables") encased within an elongated insulating body along the length of the lead. Some cables may conduct electrical signals (such as stimulating and/or sensing signals) between the pacemaker and the heart. Other cables may provide strength and/or support to the lead. The cables may extend the entire length of the lead, or a segment of that length. The elongated insulating body, generally formed of silicone or a polymer such as polyurethane, serves to simultaneously protect the cables from body fluids, and insulate the cables from one another.

A defibrillator is another example of a cardiac device that utilizes implanted elongated leads to transmit electrical signals from the defibrillator to the heart. Leads for defibrillators are generally similar to pacemaker leads, and may be affixed either internally or externally of the heart. As used herein, a "cardiac lead" may refer to either a pacemaker lead or a defibrillator lead.

While an implanted apparatus, such as a cardiac lead, may have a useful life of many years, at some point consideration may be given to extracting the lead. However, over time such leads may have become encapsulated by fibrotic tissue against the heart itself or the wall of the vein, or against other surrounding tissue. Encapsulation is especially encountered in areas where the velocity of the flow of blood is low. The fibrotic tissue can be very tough, which makes it difficult to remove the lead from the area of the heart without causing trauma to the area. When small diameter veins through which a cardiac lead passes become occluded with fibrotic tissue, separation of the lead from the vein can cause severe damage to the vein, including the possible dissection or perforation of the vein. In such cases, separation of the lead from the vein is usually not possible without restricting or containing movement of the lead, i.e., fixing the lead in position with respect to the patient, in particular, with respect to the patient's vein.

To avoid this and other possible complications, some useless cardiac leads are simply left in the patient when the pacemaker or defibrillator is removed or replaced. However, this practice can incur the risk of an undetected lead thrombosis, which can result in stroke, heart attack, or pulmonary embolism. The practice can also impair heart function, since plural leads can restrict the heart valves through which they pass. Other potential risks include obstruction of fluid flow through the vein by the inoperable lead, and migration of the lead such that it may interfere with the pacing or defibrillating function. Finally, the presence of an inoperable lead may also contribute to undesirable conditions such as septicemia or endocarditis.

Surgical removal of a cardiac lead in such circumstances often involves open heart surgery. However, open heart surgery is accompanied by significant risk and cost to the patient, as well as a potential for unintended complications. A variety of methods and apparatuses have been devised for use as alternatives to open heart surgery for cardiac lead removal. Several of these methods and apparatuses are described in related patent documents, such as U.S. Pat. No. 5,697,936, titled "Device for Removing an Elongated Structure Implanted in Biological Tissue"; U.S. Pat. No. 5,507,751, titled "Locally Flexible Dilator Sheath"; U.S. Pat. No. 5,632,749, titled "Apparatus for Removing an Elongated Structure Implanted in Biological Tissue"; U.S. Pat. No. 5,207,683, titled "Apparatus for Removing an Elongated Structure Implanted in Biological Tissue"; U.S. Pat. No. 4,943,289, titled "Apparatus for Removing an Elongated Structure Implanted in Biological Tissue"; U.S. Pat. No. 5,011,482, titled "Apparatus for Removing an Elongated Structure Implanted in Biological Tissue"; U.S. Pat. No. 5,013,310, titled "Method and Apparatus for Removing an Implanted Pacemaker Lead"; U.S. Pat. No. 4,988,347, titled "Method and Apparatus for Separating a Coiled Structure from Biological Tissue"; U.S. Pat. No. 5,423,806, titled "Laser Extractor for an Implanted Object"; U.S. Pat. No. 6,136,005, titled "Apparatus for Removing a Coiled Structure Implanted in Biological Tissue, Having Expandable Means including a Laterally Deflectable Member"; U.S. Pat. No. 6,419,974, titled "Radio Frequency Dilator Sheath", U.S. Pat. No. 6,687,548, titled "Apparatus for Removing an Elongated Structure Implanted in Biological Tissue"; U.S. Pat. No. 6,712,826, titled "Apparatus for Removing an Elongated Structure Implanted in Biological Tissue"; U.S. Pat. No. 7,359,756, titled "Apparatus for removing an Elongated Structure implanted in Biological Tissue"; U.S. Pat. No. 7,651,504, titled "Device for Removing an Elongated Structure Implanted in Biological Tissue"; U.S. Pat. No. 8,192,430, titled "Device for Extracting an Elongated Structure Implanted in Biological Tissue; U.S. Pat. Publ. No. 2005/0192591, titled "Device for removing an Elongated Structure Implanted in Biological Tissue"; U.S. Pat. Publ. No. 2006/0235431, titled "Lead Extraction Device"; U.S. Pat. Publ. No. 2010/0222787, titled "Tension Control Device"; and U.S. Pat. Publ. No. 2011/0238078, titled "Device and Method for Positioning an Implanted Structure to Facilitate Removal", among others. Each of the aforementioned patents and publications is incorporated by reference as if fully set forth herein.

Although the prior art devices have been found to be reasonably effective in many situations, physicians continue to encounter problematic situations in which existing extraction devices may not perform as efficiently as desired for lead removal, and/or in which the capability of the device to remove the lead could be enhanced by preparing the lead for removal prior to entry of the extraction device into the body passageway.

One such instance involves the removal of an implanted apparatus, such as a cardiac lead as described above having one or more cables, etc., extending along a length of the apparatus. After such apparatuses have been implanted for a period of time, the cables can work their way through the insulating material, such that they extend outwardly, or laterally, of the main body of the implanted apparatus along this length. This arrangement may hamper the ability of the physician to advance an extraction device over the proximal end of the implanted apparatus, as the laterally extending cable may be positioned in a manner such that it is not easily captured within the extraction device as that device tracks along the outer surface of the apparatus.

It would be desirable to provide a device that is capable of arranging the proximal end of the implanted apparatus in a manner to facilitate advancement of an extraction device thereover, and to facilitate extraction of the implanted apparatus from encapsulating tissue in the body passageway.

BRIEF SUMMARY

The problems of the prior art are addressed by the features of the present invention. In one form thereof, the invention comprises a device for preparing an implanted medical apparatus for extraction from the body of a patient. The device includes a first handle and a second handle, wherein the first handle has a surface for receiving the implanted medical apparatus therealong. A wire member having a first end and a second end is positioned to span a distance between the surface of the first handle, and the second handle. The wire member first end is removably engaged with the first handle, and the wire member second end is removably engaged with the second handle. The wire member is sized and arranged to enable the wire member to be wound around a length of the implanted medical apparatus.

In another form thereof, the invention comprises an assembly for removal of an implanted cardiac lead from a body passageway of a patient. The assembly includes a first handle and a second handle. Each of the handles comprises a handle body having a ledge surface configured for receiving a length of the cardiac lead therealong. Each of the handle bodies has a channel extending inwardly from the ledge into an interior of the handle body, and has an aperture communicating with the channel. Each handle further comprises a tab having a first end and a second end. The tab first end is engaged with the handle body, and the tab second end has a pin member engaged therewith. The pin member is removably receivable in the channel via the aperture. A wire member has a first end and a second end. The wire member first end is received in the channel of the first handle through an opening in the ledge surface, and is configured and arranged to be maintained in the channel when the pin member is received therein. The wire member second end is received in the channel of the second handle through an opening in the ledge surface, and is configured and arranged to be maintained in the channel when the pin member is received therein. The wire member is dimensioned to span a distance between the respective ledge surfaces.

In yet another form thereof, the invention comprises a method for preparing an elongated implanted medical apparatus for extraction from the body of a patient. A device for preparing the elongated implanted apparatus for extraction is positioned for engagement with a free end of the elongated implanted medical apparatus. The device comprises a first handle, a second handle, and a wire member spanning a distance between the handles. The wire member has a first end removably engaged with the first handle, and a second end removably engaged with the second handle. The elongated implanted apparatus is aligned along a surface of the first handle. The second handle is wound around a length of the elongated implanted apparatus in a proximal direction from the first handle, such that the wire is wrapped around said length. The first and second handles are then removed from the wire wrapped around the length of the elongated implanted apparatus.

DETAILED DESCRIPTION OF THE DRAWINGS AND THE PRESENTLY PREFERRED EMBODIMENTS

Figure 1:
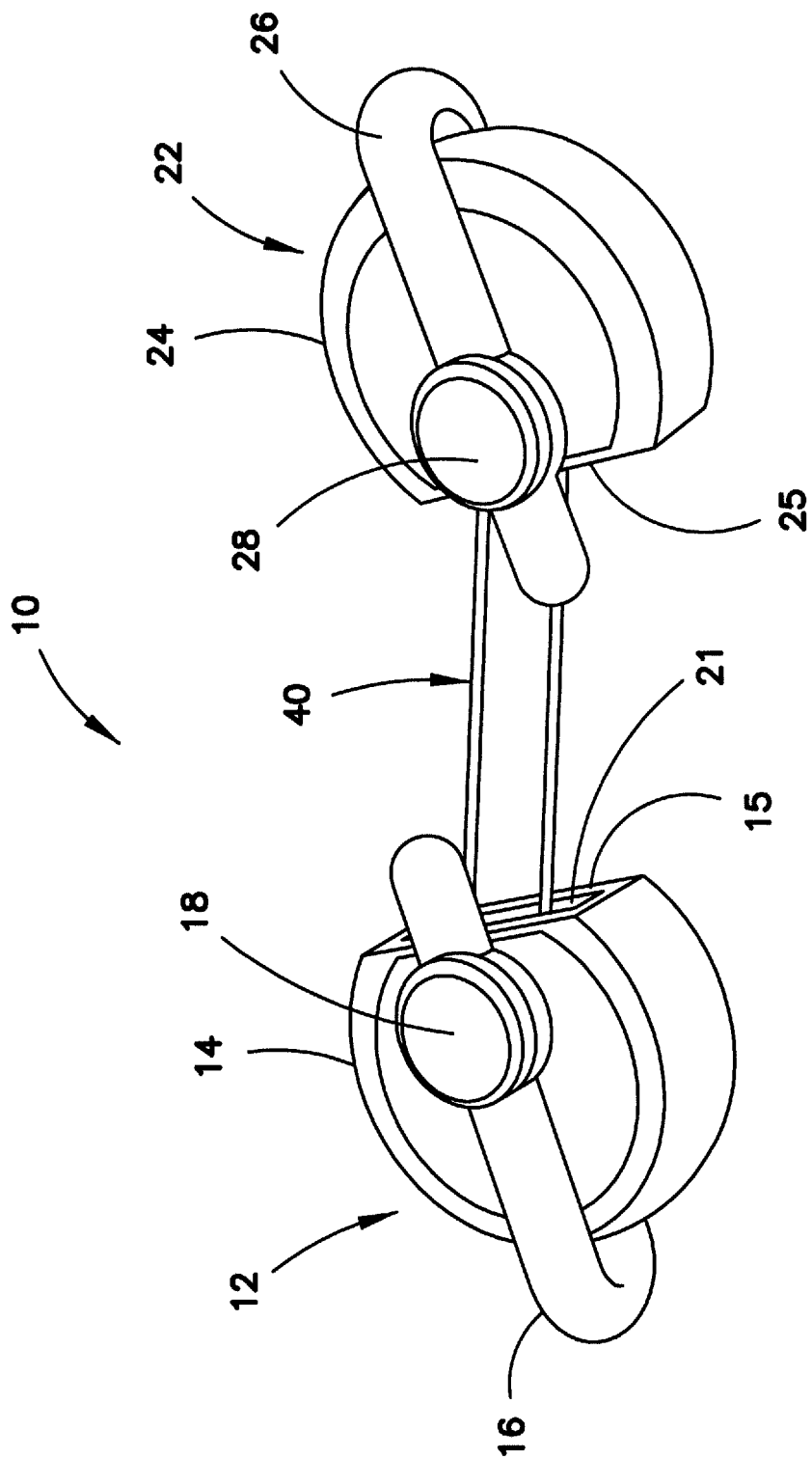
FIG. 1 is a side view of one example of a device for preparing an implanted medical apparatus for extraction.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. It is understood that like-referenced numerals are used throughout the figures to designate similar components.

Throughout the specification, when referring to a medical device, or a portion of a device, the terms "distal" and "distally" denote a position, direction, or orientation that is generally toward, or in the direction of, the patient when the device is in use. The terms "proximal" and "proximally"

denote a position, direction, or orientation that is generally away from the patient, or in the direction of the operator, during use of the device.

Figure 2:
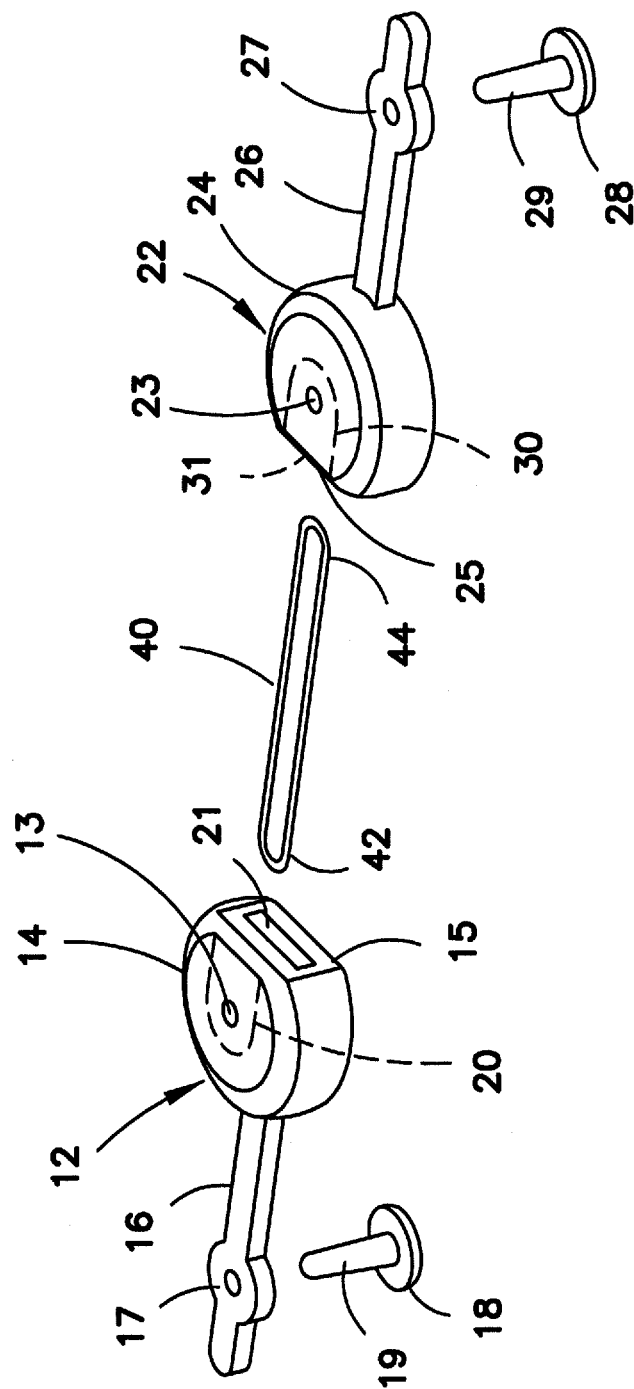
FIG. 2 is an exploded view of the device of FIG. 1.

FIG. 1 illustrates a side view of one example of a device 10 for preparing an implanted medical apparatus for extraction. FIG. 2 is an exploded view of the device of FIG. 1.

As illustrated, device 10 includes a pair of handles 12, 22. Each handle includes a handle body 14, 24 having a surface, such as ledge 15, 25, configured for receiving a length of the implanted apparatus along the surface. A tab 16, 26 extends from handle body 14, 24, preferably at an opposite end of the handle body from ledge 15, 25. Tab 16, 26 includes an aperture 17, 27 for receiving pin 18, 28. Alternatively, the pin may be integral with the tab. Upon assembly of device 10, an extension 19, 29 of pin 18, 28 is received in a suitably-sized opening 13, 23 in the handle body, as further described herein.

Each main body 14, 24 includes a channel 20, 30 inwardly directed from a slot 21, 31 along ledge 15, 25. Channel 20, 30 extends rearwardly along main body 14, 24 from slot 21, 31 to a distance beyond handle body opening 13, 23. Although only slot 21 is visible in the orientation of FIG. 2, slot 31 and the rearward extension of channels 20, 30 may be visualized by the phantom lines in FIG. 2.

Handles 12, 22 are joined by a generally flexible joinder member, such as wire 40. In the illustrated example, wire 40 has the general configuration of a rubber band, or a rectangle having rounded ends 42, 44. In the example shown, each one of ends 42, 44 is received through a respective one of slots 21, 31, and extends into a respective channel 20, 30.

During assembly of device 10, each pin 18, 28 is aligned with a respective tab aperture 17, 27, such that pin extension 19, 29 extends through the aperture. Each tab 16, 26 is pivoted such that pin extension 19, 29 is received in an appropriate one of openings 13, 23 as described above, and thereby maintains the position of wire ends 42, 44 in the respective channel 20, 30. The assembled device is shown in FIG. 1.

Those skilled in the art will appreciate that handles may be formed (e.g., by molding) from a variety of compositions, such as rigid plastics, and thermoplastic rubbers such as SANTOPRENE®. The tabs and pins may be formed from a more flexible composition, such as an acrylonitrile butadiene styrene (ABS) that is bondable to SANTOPRENE®. The wire may be formed from various compositions, such as metals and metal alloys, having the strength and flexibility to enable the wire to be wound around the implanted structure targeted for extraction, and to maintain its wound configuration following removal of the handles. One particularly preferred example is a stainless steel composition that has been annealed to remove the spring tension from the wire.

Wire 40 will preferably be dimensioned such that respective ledges 15, 25 are about 1 to 3 inches (2.54 to 7.62 cm) apart in the assembled device shown in FIG. 1, and more preferably, about 2 inches (5.08 cm) apart. Those skilled in the art will appreciate that a wire of greater, or of lesser, dimensions may be used in a particular case, but it is believed that a wire having the dimensions recited herein will suffice for most applications.

Use of device 10 to prepare an implanted medical apparatus for extraction from the body of a patient may be further understood upon a discussion of FIGS. 3-7. Initially, a proximal end 102 of the implanted lead 100 is severed from the pacemaker, defibrillator, etc., in a manner such that it is accessible to the operator. If the lead is of a type having a lumen extending therethrough, a locking stylet 120 may be inserted into the lumen of the lead. Locking stylets are well known devices for use during the extraction of cardiac leads of the type having a lumen therethrough, and are further described, e.g., in the incorporated-by-reference U.S. Pat. Nos. 4,943,289 and 5,207,683.

Figure 3:
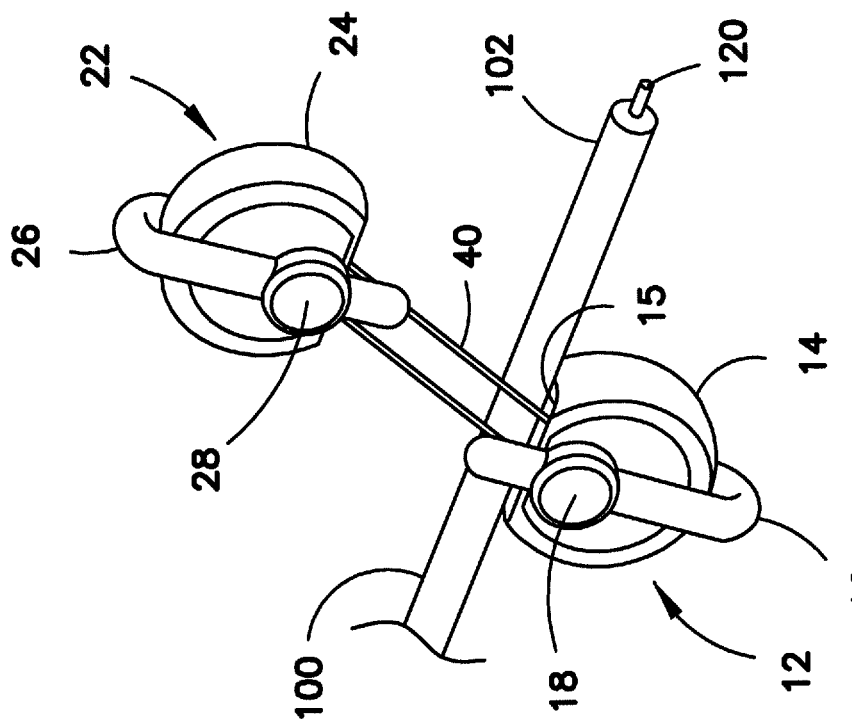
FIG. 3 illustrates a cardiac lead received along a surface of the device.
Figure 3A:
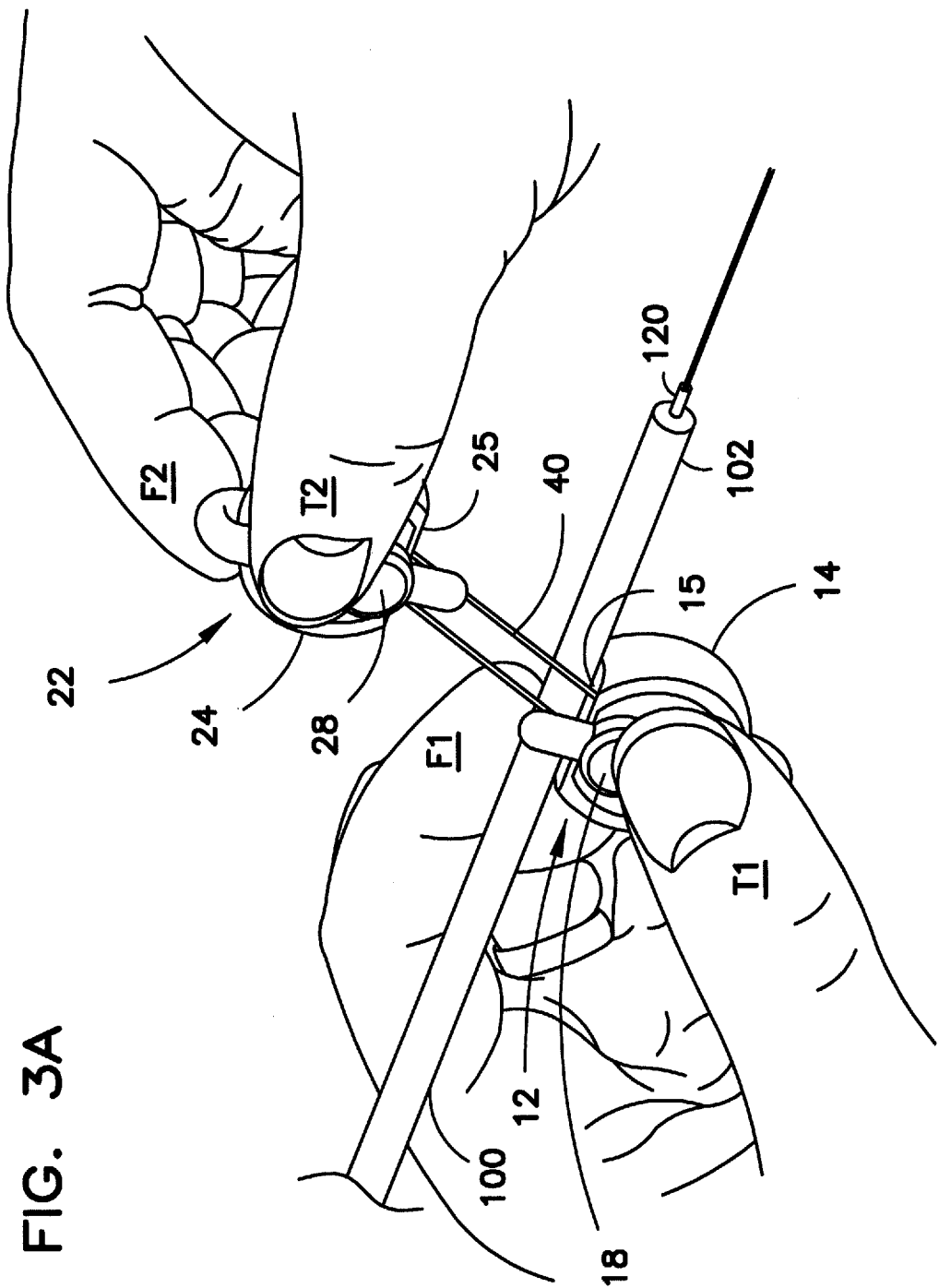
FIG. 3A illustrates the hands of an operator positioning the cardiac lead along the device shown in FIG. 3.

In this example, device 10 is arranged such that the cardiac lead intended for removal is positioned along the ledge of one of the handles. As shown in FIG. 3, lead 100 is positioned along ledge 15 of handle 12. As further shown in FIG. 3A, the operator may hold lead 100 against the ledge with a forefinger F1 and maintain control of the handle with the thumb T1 of the same hand. The operator then grasps handle 22 between the forefinger F2 and thumb T2 of the other hand.

Figure 4:
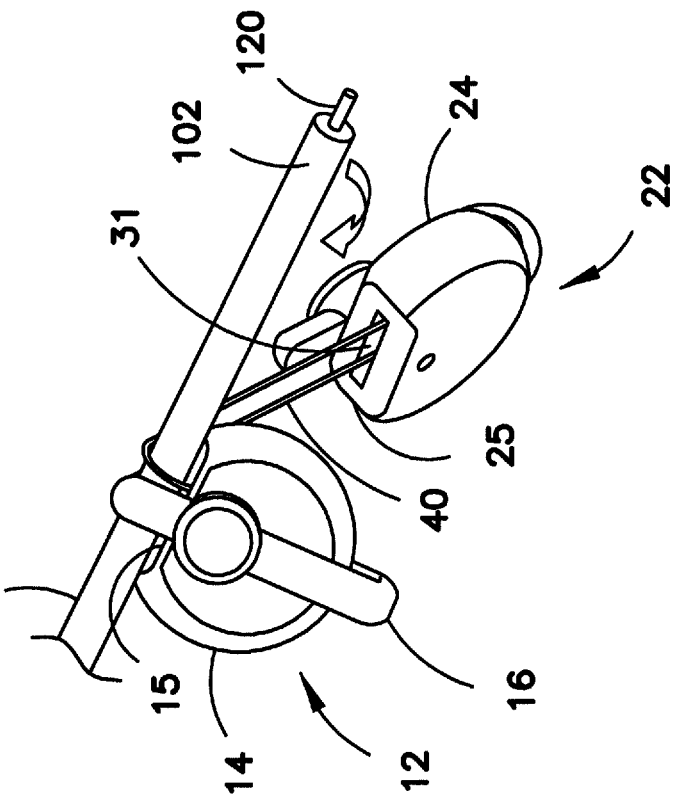
FIGS. 4 and 5 illustrate successive stages of winding the device around the cardiac lead.
Figure 5:
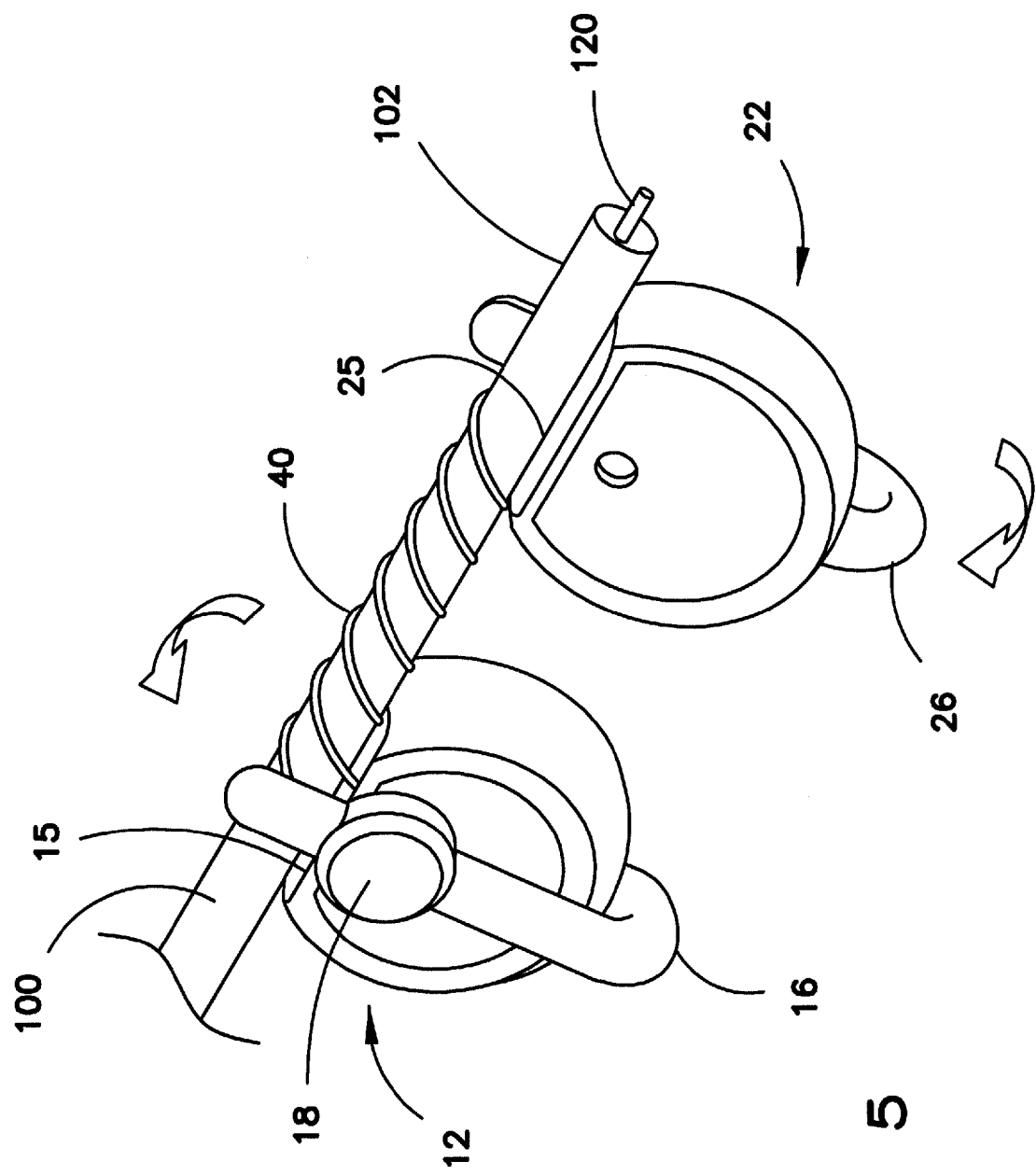

While continuing to hold lead 100 in place on ledge 15, wire 40 is wound around lead L in the proximal direction by winding handle 22 around the lead, as shown in FIG. 4. While winding wire 40 around lead 100, each of tabs 16, 26 will typically be pointing in the general direction of the lead. The operator continues to wind handle 22 around lead 100 until wire 40 is completely wrapped around the lead, as shown in FIG. 5. At this time, both handles 12, 22 can be further wound in opposing directions around lead 100, as indicated by the arrows in FIG. 5, to tightly compress wire 40 around the lead.

Figure 6:
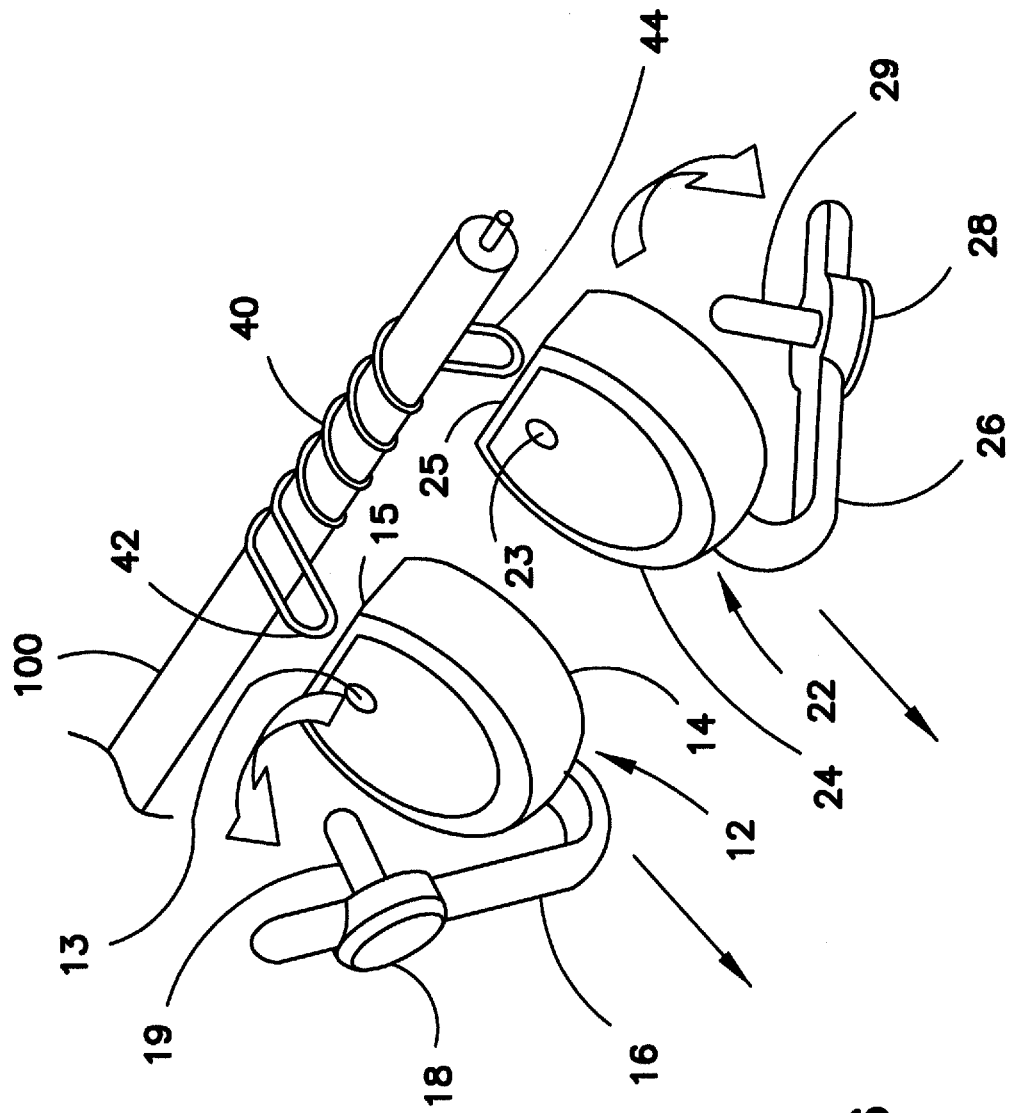
FIG. 6 illustrates the release of the device handles from the lead.
Figure 7:
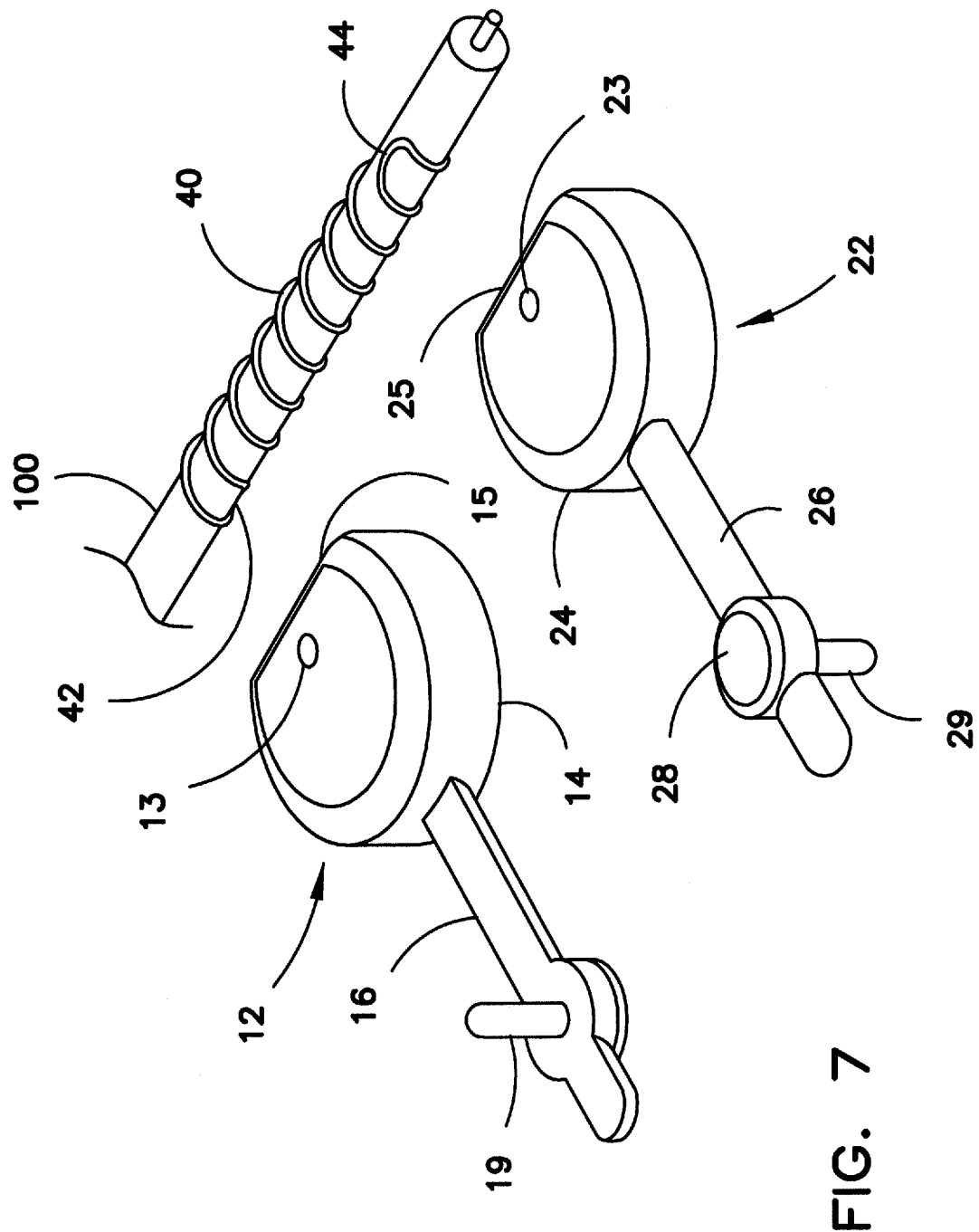
FIG. 7 illustrates the handles as released from the device, and the compression of the ends of the wire around the lead.

Once wire 40 has been fully compressed around the lead, tabs 16, 26 are pivoted such that each pin 18, 28 is removed from a respective handle body opening 13, 23. This action frees wire ends 42, 44 from the respective channel 20, 30, as shown in FIG. 6. Handles 12, 22 may then be removed, and wire ends 42, 44 may be squeezed or otherwise compressed around the lead 100. The lack of spring tension in the annealed wire enables the respective axial ends of the wire to remain compressed against the lead as shown in FIG. 7. As shown in FIG. 7, the proximal end of lead 100 has now been prepared for extraction, e.g., by passage thereover of a conventional lead extraction device, such as the device disclosed in the incorporated-by-reference U.S. Pat. Publ. No. 2006/0235431.

Those skilled in the art recognize that many elongated implanted medical apparatuses, such as a cardiac (e.g. pacemaker or defibrillator) lead, intended for removal include one or more cables, wires, coils, and the like ("cables") that extend along the length of the implanted lead, or a portion of that length. As stated above, conventional lead removal devices are typically introduced over a proximal end of the lead that has previously been cut from the cardiac device. However, in some cases one or more of the cables may have worked their way through the insulation or other outer surface of the implanted lead. Many factors can cause a cable to work its way through the outer surface of a cardiac lead, such as the body environment in which the lead is positioned, the length of time in which the lead has been implanted, the degree of curvature of the vessel in which the lead has resided, etc.

It may be difficult, if not impossible, to properly advance the tip of the extraction or removal device over such a lead, so that the extraction device simultaneously advances over both the lead and any laterally-extending cable(s). Even when such positioning is possible, it may require additional unintended effort by the physician and/or other medical personnel, and may require additional surgical time and expense to accomplish the extraction.

In order to avoid these disadvantages, it is beneficial to manage, arrange, or otherwise position the proximal end of the implanted lead such that cables do not protrude in a lateral direction from the lead during advancement of the extraction device. Rather, it is desirous that the cables are brought back into substantial contact with the portion of the lead over which the lead extraction device is to be advanced. Even if no known cable separation has taken place, it may still be advantageous to manage at least the proximal end of the implanted apparatus in the manner described, and as shown in the example of FIGS. 3-7. This action would minimize the likelihood of any such separation occurring during a lead removal procedure, or would bring the cable back into contact with the lead in the event that an unknown separation had occurred.

Figure 9:
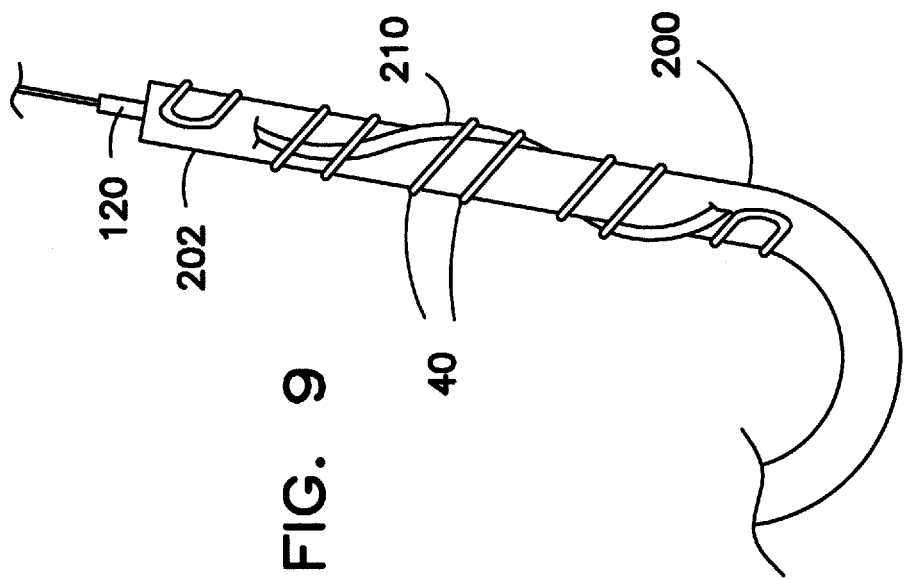
FIG. 9 illustrates the lead and cable of FIG. 8, and further illustrates a wire wound around the lead and cable.
Figure 8:
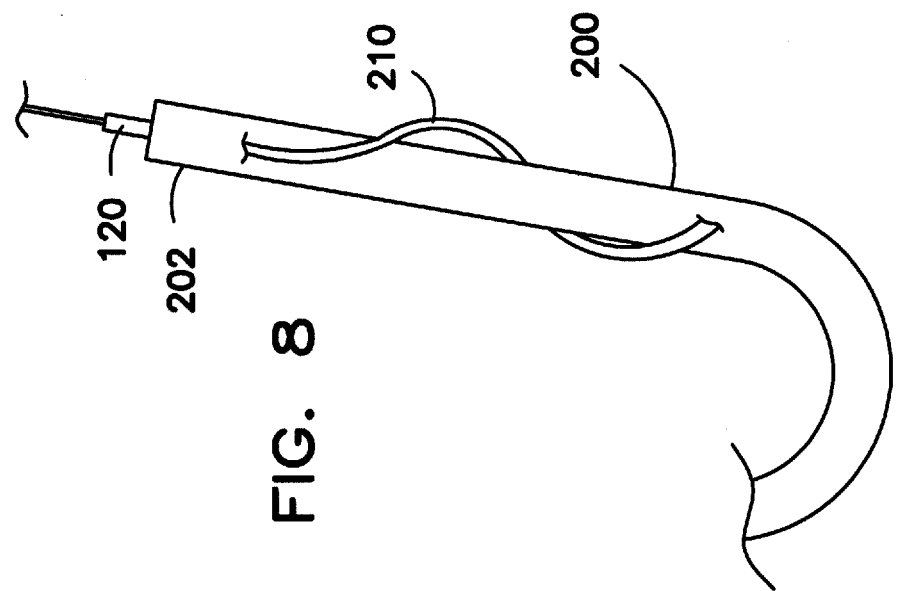
FIG. 8 is a view of a proximal end portion of an implanted cardiac lead intended for extraction from a body vessel, and illustrating a cable protruding through the outer insulating portion of the lead.
Figure 10:
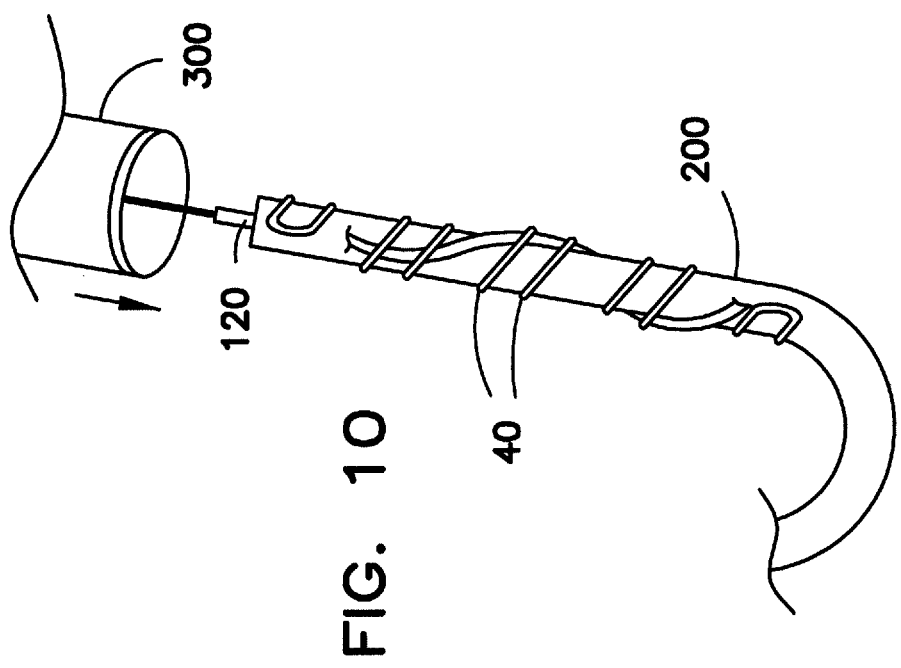
FIG. 10 illustrates the lead, cable, and wire of FIG. 9, and further illustrates an end of a lead extraction device arranged for passage over the proximal end of the lead segment of FIG. 9.

FIGS. 8-10 illustrate another example of the management of a severed proximal end 202 of a lead 200 utilizing device 10. In this example, a cable 210 has worked its way through a length of the outer surface of the lead. Other than illustrating a cable protruding therethrough, lead 200 is otherwise similar to lead 100 in the example of FIGS. 3-7. Although the example of FIG. 8 illustrates a single cable 210 protruding from a discrete portion of lead 200, those skilled in the art will appreciate that a lead intended for extraction may have more than one cable protruding therefrom, which cable(s) may protrude from different lengths of the lead.

FIG. 9 illustrates lead 200 after wire 40 has been wrapped around cable 210, e.g., in the manner described above with reference to FIGS. 3-7. As shown, wire 40 brings cable 210 into close contact with the exterior surface of the lead. FIG. 10 illustrates the lead and wire of FIG. 9, and also illustrates a lead extraction device 300 positioned for advancement over lead 200. As stated above, lead extraction devices are well-known in the art, and the skilled artisan can readily select a suitable extraction device for use in a particular extraction operation wherein wire 40 is wrapped around the lead. By bringing cable 210 in close proximity to the body of lead 200 prior to advancement of extraction device 300 over the lead, the extraction device readily advances over the entire lead structure, and is not hindered in such advancement by the present of a laterally-extending cable or like element.

Figure 11:
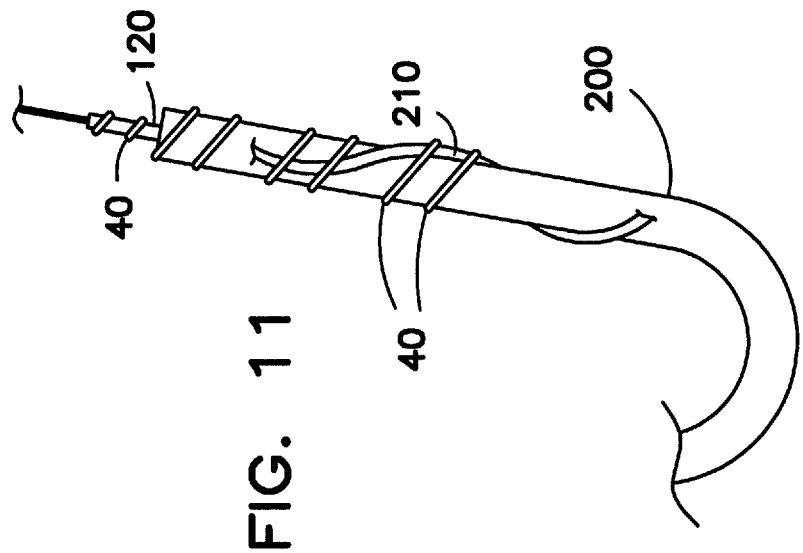
FIG. 11 illustrates the lead, cable, and wire as in FIG. 9, wherein the wire is also wound around a locking stylet.

FIG. 11 illustrates a variation of the example of FIGS. 8-10. In this variation, wire 40 is also wrapped around locking stylet 120. When a cardiac lead has a lumen extending therethrough as described, it may be advantageous to pass a locking stylet into the lumen in well-known fashion. In some instances the locking stylet may not fully lock with the lead when introduced into the lumen, thereby causing the stylet to slip or otherwise disengage when pulled. By wrapping the wire of device 10 around the lead and the stylet as shown in the figure, an unintended withdrawal or disengagement of the locking stylet from the lead is prevented. Additionally, this arrangement establishes an additional locking point on the lead, thereby allowing for better overall control of the lead.

Figure 12:
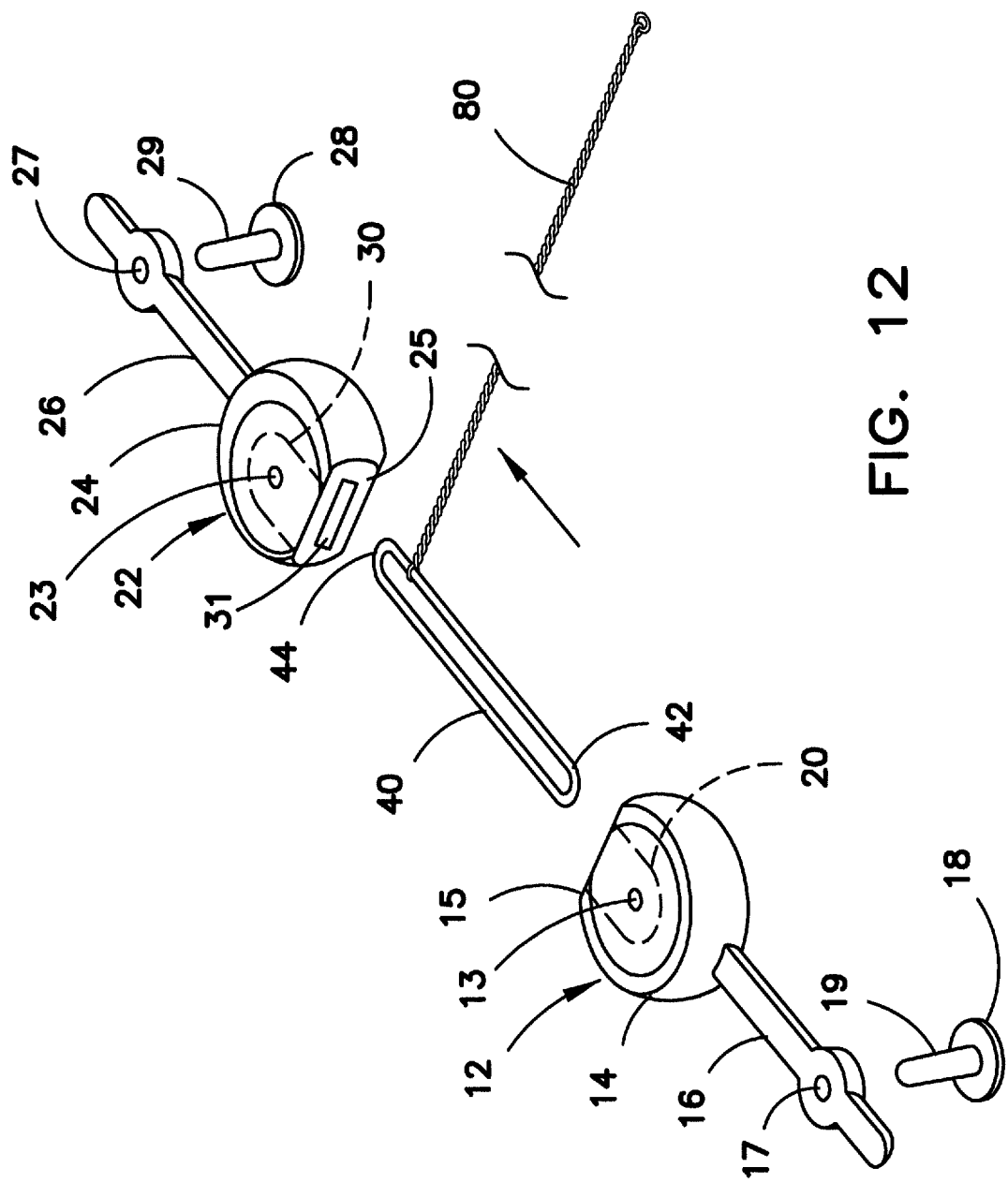
FIG. 12 is an exploded view of the device as shown in FIG. 2, including a tether engaged with the wire.
Figure 13:
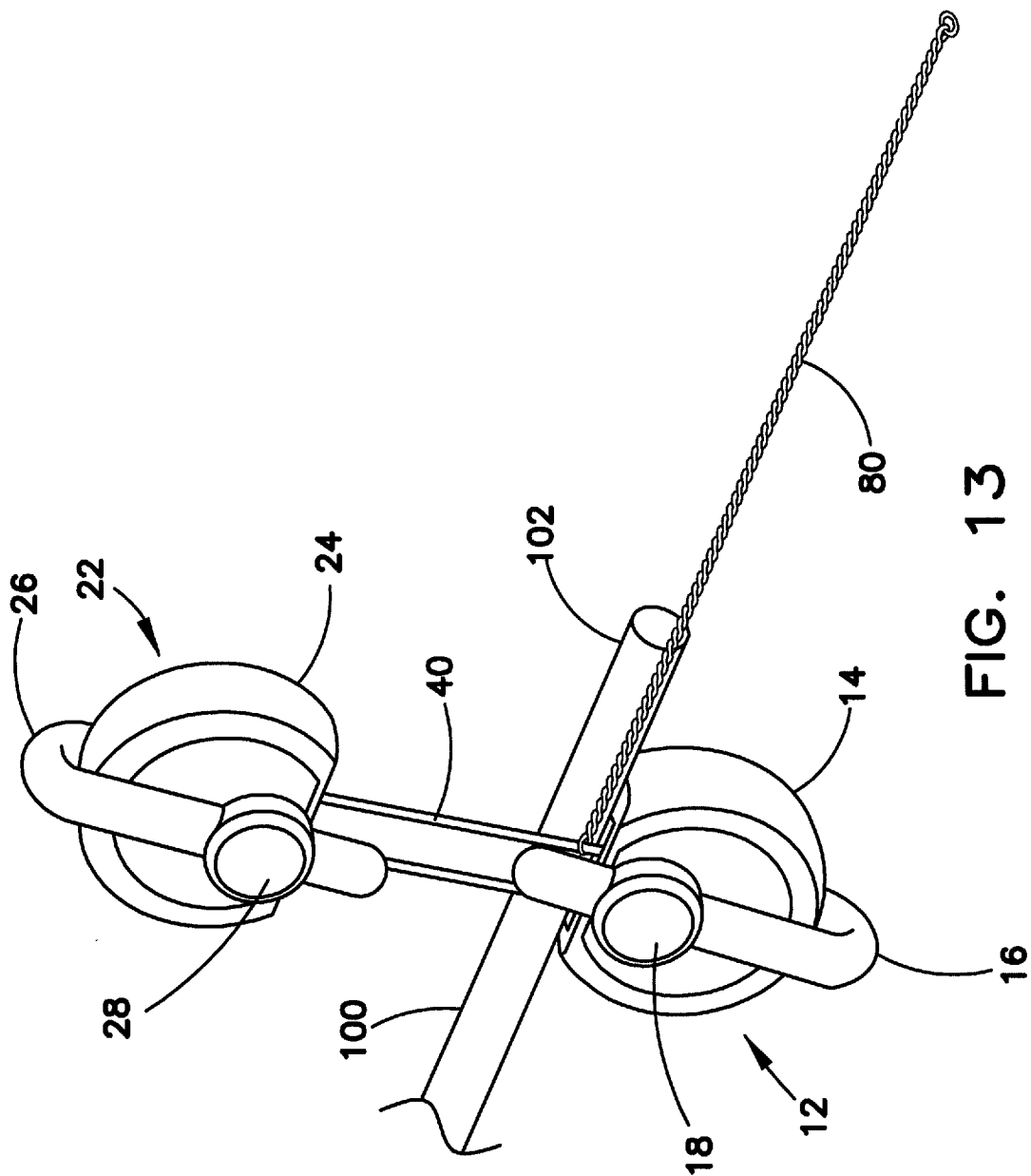
FIG. 13 illustrates a cardiac lead received along a surface of the device as shown in FIG. 3, illustrating the tether engaged with the wire.

Another variation of device 10 is illustrated in FIGS. 12 and 13. In this variation, a tether 80 is engaged with wire 40. FIG. 12 is an exploded view of device 10, as in FIG. 2, wherein tether 80 extends from wire 40. FIG. 13 illustrates a cardiac lead received along a surface of the device, in the same general manner as FIG. 3. A tether may be useful, e.g., in cases wherein a lumenless lead is being extracted, and/or in cases in which the lead has a lumen extending therethrough and yet it may not be practical to utilize a locking stylet. Tether 80 can be formed of the same composition as wire 40. The tether will generally have a length to enable it to extend through and beyond the extraction device.

Those skilled in the art will appreciate that the described features of device 10 need not have the specific configuration shown in the examples. For example, handle bodies 14, 24 need not necessarily have generally flat ledges 15, 25 as shown. Rather, the handle bodies may have a gentle curvature, and in some instances may even have a groove, channel, or like structure, as long as the implanted apparatus, such as lead 100, may be controllably received along a surface of the handle. Further, although there may be manufacturing economy in providing two identical handles, this is not required, and the respective handles may have different configurations. In some instances, only one handle (such as handle 12 in the figures) need have a ledge or other surface for receiving the implanted apparatus therealong.

Similarly, handles 12, 22, need not be rounded as shown, as other geometrically shaped handles will also function in the manner as the handles shown. Similarly, tabs 16, 26 need not necessarily be integral with the handle bodies, as non-integral tabs and like structures will normally be capable of being positioned in like manner to carry out the functions of the tabs as described.

Those skilled in the art will also appreciate that device 10 may also find other uses in the medical field. For example, if it is desirous to remove a tenaciously-calcified implanted structure, such as an infusion catheter, from a vessel, a locking stylet-like device or a balloon-tipped removal device may be arranged to engage the distal portion of the structure in well-known manner. In this case, device 10 can be arranged to couple the proximal end of the structure to the removal device. As a result, the physician can extract the implanted structure by pulling on only one device.

It is intended that the foregoing detailed description be regarded as illustrative rather than limiting, and that it be understood that it is the following claims, including all equivalents, that are intended to define the spirit and scope of this invention.

The invention claimed is:

1. A method for preparing an elongated implanted medical apparatus for extraction from the body of a patient, comprising:
    positioning a device for engagement with a free end of the elongated implanted medical apparatus, the device comprising a first handle, a second handle, and a wire member spanning a distance between the handles, the wire member having a first end removably engaged with the first handle and a second end removably engaged with the second handle;
    aligning the elongated implanted apparatus along a surface of the first handle;
    winding the second handle around a length of the elongated implanted apparatus in a proximal direction from the first handle such that the wire is wrapped around said length; and
    removing said first and second handles from said wire wrapped around said length of the elongated implanted apparatus.

2. The method of claim 1, wherein the surface of the first handle comprises a ledge, and the implanted apparatus is aligned along said ledge of the first handle.

3. The method of claim 1, wherein the elongated implanted apparatus comprises a cardiac lead having one or more cables extending therein, at least one of said cables extending laterally through an outer surface of said cardiac lead, and wherein said winding step comprises wrapping the wire around said cardiac lead and said laterally extending cable.

4. The method of claim 3, wherein said cardiac lead includes a lumen extending therein, further comprising a step of introducing a first end of a locking stylet into said lumen, and wherein said winding step comprises wrapping the wire around the cardiac lead, the laterally extending cable, and a second end of the locking stylet.

5. The method of claim 4, further comprising a step of advancing a lead extraction device over the cardiac lead, laterally extending cable, and second end of the locking stylet having said wire wrapped therearound.

* * * * *